(12) United States Patent
Bedoukian

(10) Patent No.: US 10,111,429 B2
(45) Date of Patent: *Oct. 30, 2018

(54) FEEDING DETERRENCE IN AGRICULTURAL PESTS SUCH AS HEMIPTERA, LEPIDOPTERA AND COLEOPTERA

(71) Applicant: BEDOUKIAN RESEARCH, INC., Danbury, CT (US)

(72) Inventor: Robert H. Bedoukian, West Redding, CT (US)

(73) Assignee: BEDOUKIAN RESEARCH, INC., Danbury, CT (US)

(*) Notice: Subject to any disclaimer, the term of this patent is extended or adjusted under 35 U.S.C. 154(b) by 112 days.

This patent is subject to a terminal disclaimer.

(21) Appl. No.: 14/390,826

(22) PCT Filed: Apr. 30, 2013

(86) PCT No.: PCT/US2013/000120
§ 371 (c)(1),
(2) Date: Oct. 6, 2014

(87) PCT Pub. No.: WO2013/165476
PCT Pub. Date: Nov. 7, 2013

(65) Prior Publication Data
US 2015/0051276 A1 Feb. 19, 2015

Related U.S. Application Data

(60) Provisional application No. 61/687,920, filed on May 2, 2012.

(51) Int. Cl.
| | | |
|---|---|---|
| A01N 31/06 | (2006.01) | |
| A01N 35/06 | (2006.01) | |
| A01N 37/02 | (2006.01) | |
| A01N 37/06 | (2006.01) | |
| A01N 37/18 | (2006.01) | |
| A01N 37/36 | (2006.01) | |
| A01N 37/42 | (2006.01) | |
| A01N 43/08 | (2006.01) | |
| A01N 43/16 | (2006.01) | |
| A01N 49/00 | (2006.01) | |

(52) U.S. Cl.
CPC ............ *A01N 43/16* (2013.01); *A01N 31/06* (2013.01); *A01N 35/06* (2013.01); *A01N 37/02* (2013.01); *A01N 37/06* (2013.01); *A01N 37/18* (2013.01); *A01N 37/36* (2013.01); *A01N 37/42* (2013.01); *A01N 43/08* (2013.01); *A01N 49/00* (2013.01)

(58) Field of Classification Search
CPC combination set(s) only.
See application file for complete search history.

(56) References Cited

U.S. PATENT DOCUMENTS

| 4,332,941 A | 6/1982 | Berthold et al. |
| 5,118,711 A | 6/1992 | Wilson et al. |
| (Continued) | | |

FOREIGN PATENT DOCUMENTS

| JP | 63-48203 | 2/1988 |
| JP | 2-131405 | 5/1990 |
| (Continued) | | |

OTHER PUBLICATIONS

Nauen et al. "Thiamethoxam is a neonicotinoid precursor converted to clothianidin in insects and plants" Pesticide Biochemistry and Physiology, 2003, vol. 76, pp. 55-69.*

(Continued)

*Primary Examiner* — Kendra D Carter
(74) *Attorney, Agent, or Firm* — Ohlandt, Greeley, Ruggiero & Perle, L.L.P.

(57) ABSTRACT

Compounds are used as agents that deter feeding of crops by agricultural pests such as hemiptera, lepidoptera and coleoptera, including, but not limited to, stink bugs, codling moth larvae and granary weevils. Feeding deterrence is obtained by contact of the insects with at least one of the compounds of the structure (I) wherein R is —OH, =O, —OC(O)$R_4$, —O$R_6$, or —(O$R_6$)$_2$, wherein each $R_6$, is independently an alkyl group containing from 1 to 4 carbon atoms and $R_4$ is a branched or straight chain, saturated or unsaturated, hydrocarbyl group with zero to two double bonds and from 1 to 15 carbon atoms; X is O or $CH_2$ with the proviso that when X is OR can only be =O; each Z is independently (CH) or ($CH_2$); y is a numeral selected from 1 and 2; $R_1$ is H or a branched or straight chain, saturated or unsaturated hydrocarbyl group with zero to two double bonds and from 1 to 15 carbon atoms; $R_2$ is H or a branched or straight chain, saturated or unsaturated hydrocarbyl group with zero to three double bonds and from 1 to 15 carbon atoms; $R_3$ is selected from H, a branched or straight chain, saturated or unsaturated hydrocarbyl group with zero to three double bonds and from 1 to 15 carbon atoms, —(CH2)$_n$OH, —C(O)O$R_5$, —$CH_2$C(O)O$R_7$, —$CH_2$C(O)$R_8$, —C(O)N$R_9R_{10}$, and —$CH_2$C(O)N$R_{11}R_{12}$ where each of $R_5$, $R_7$, $R_8$, $R_9$, $R_{10}$, $R_{11}$ and $R_{12}$ is independently selected from H and a branched or straight chain, saturated or unsaturated hydrocarbyl group with zero to three double bonds and from 1 to 15 carbon atoms and n is an integer of from 1 to 12; the bond between the 2 and 3 positions in the ring structure may be a single or a double bond; and wherein the compounds of structure (I) contain from 9 to 20 total carbon atoms in the compounds.

(I)

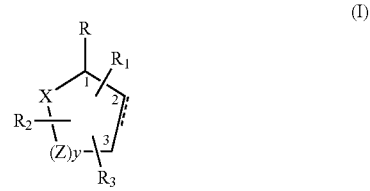

9 Claims, No Drawings

(56) References Cited

U.S. PATENT DOCUMENTS

| | | | |
|---|---|---|---|
| 6,060,507 | A | 5/2000 | Hill et al. |
| 7,622,498 | B2 | 11/2009 | Justino et al. |
| 8,551,510 | B2 | 10/2013 | Bedoukian |
| 2010/0278755 | A1 | 11/2010 | Dell |
| 2011/0124877 | A1 | 5/2011 | Ito et al. |
| 2012/0046359 | A1 | 2/2012 | Bedoukian |
| 2012/0076674 | A1 | 3/2012 | Nomura et al. |
| 2012/0077674 | A1 | 3/2012 | Cargeeg et al. |

FOREIGN PATENT DOCUMENTS

| | | | |
|---|---|---|---|
| JP | 4-164079 | | 6/1992 |
| JP | 5-178706 | | 7/1993 |
| JP | 7-138102 | | 5/1995 |
| JP | 2002-356404 | | 12/2002 |
| JP | 2005-41805 | A | 2/2005 |
| JP | 2005-162730 | | 6/2005 |
| JP | 2007-502860 | | 2/2007 |
| JP | 2009-256311 | | 11/2009 |
| JP | 2009-542789 | | 12/2009 |
| JP | 2013/126960 | | 6/2013 |
| WO | 01/41568 | A2 | 6/2001 |
| WO | 2004/100971 | A1 | 11/2004 |
| WO | 2008/007100 | A2 | 1/2008 |
| WO | WO 2008012756 | A2 * | 1/2008 ............ A01N 37/02 |
| WO | 2009049378 | A1 | 4/2009 |
| WO | 2012/047608 | A2 | 4/2012 |

OTHER PUBLICATIONS

Sheridan, R.P. "The Most Common Chemical Replacements in Drug-Like Compounds" J Chem. Inf. Comput. Sci., 2002, vol. 42, pp. 103-108.*

Szczepanik et al. "The Effect of alpha-Methylenelactone Group on the Feeding Deterrent Activity of Natrual and Synthetic Alkenes Against Colorado Potato Beetle, Lepinotarsa decemlineata Say" Polish J. of Environ.Stud., 2009, vol. 18, No. 6, pp. 1107-1112.*

Gabrys et al. "Environmentally Safe Insect Control: Feeding Deterrent Activity of Alyl-Substituted gamma- and delta-Lactones to Peach Potato Aphid and Colorado Potato Beetle" Polish J. of Environ.Stud., 2006,, vol. 15, No. 4, pp. 549-556.*

J. G. Cannon Chapter Nineteen in Burger's Medicinal Chemistry and Drug Discovery, Fifth Edition, vol. I: Principles and Practice, Wiley-Interscience 1995, pp. 783-802, 784.*

Japanese Office Action dated Feb. 23, 2016 from corresponding Japanese Application No. JP-2015-510248, 10 pages.

First Office Action, with translation, dated Oct. 27, 2015 from corresponding Chinese Application No. 201380022820.4, 16 pages.

Chunfu et al.; "Effect of Induced Resistance of Larix gmelinii on Growth and Development of Lymantria dispar"; Journal of Northeast Forestry University; May 2010; vol. 38, No. 5, 2 pages.

Dettner et al; "Defensive Secretions of Three Oxytelinae Rove Beetles (*Coleoptera: Staphylinidae*)"; Journal of Chemical Ecology; Mar. 1982; vol. 8, No. 11, 10 pages.

Chinese Office Action dated May 4, 2016 from corresponding Chinese Patent Application No. 201380022820.4, 12 pages.

International Search Report dated Jul. 10, 2013 from PCT/US2013/000120, 3 pages.

Written Opinion dated Jul. 10, 2013 from PCT/US2013/000120, 15 pages.

Chinese Third Office Action dated Oct. 10, 2016 from corresponding Chinese Patent Application No. 201380022820.4, 18 pages.

European Extended Search Report dated Oct. 21, 2016 from corresponding European Patent Application No. 13784833.9, 16 pages.

Brunissen et al.; "Effects of systemic potato response to wounding and jasmonate on the aphid Macrosiphum euphorbiae (*Sternorryncha: Aphididae*)", J Appl Entomol, 134, 2010, pp. 562-571.

Dancewicz et al.; "Effect of Oxygen Incorporation Into Cyclohexanone Ring on Antifeedant Activity", Journal of Plant Protection Research, vol. 51, No. 1, 2011, pp. 23-28.

Dancewicz et al.; "Feeding Deterrent Activity of α-Methylenelactones to PEA Aphid Acyrthosiphon Pisum (Harris) and Green Peach Aphid Myzus Persicae (Sulzer)"; Polish Journal of Natural Sciences, 2006, No. 20(1); pp. 23-31.

Gabrys et al.; "Environmentally Safe Insect Control: Feeding Deterrent Activity of Alkyl-Substituted γ- and δ-Lactones to Peach Potato Aphid (*Myzus persicae* [Sulz.]) and Colorado Potato Beetle (*Leptinotarsa decemlineata* Say)", Polish Journal of Environmental Studies, vol. 15, No. 4, 2006, pp. 549-556.

Mosandl et al.; "Stereoisomeric Flavor Compounds. 20.1 Structure and Properties of γ-Lactone Enantiomers"; J. Agric. Food. Chem., 1989, 37, pp. 413-418.

IPRP dated Nov. 13, 2014 from corresponding PCT Application No. PCT/US2013/000120, 10 pages.

Barsevškis et al"Elater ferrugineus Linnaeus 1758 (*Coleoptera Elateridae*)—a new species for the fauna of Latvia" Dec. 31, 2011 URL: https://www.reserachgate.net/profile/Arvds_Barsevskis/publication/236003007_Elater-ferrugineus_Linnaeus-1758-(Coleoptera-Elateridae)-a-new-species-for-the-fauna-of-Latvia.pdf (retrieved on Feb. 8, 2018.

Devanand Lakshmichand Luthria et al. "Insect Antifeedant Activity of Furochromones: Structure-Activity Relationships" Journal of Natural Products., vol. 56, No. 5 May 1, 1993 pp. 671-675, American Chemical Society, Washington, D.C. US.

Ômura et al. "Floral Scent of Osmathus fragrans Discourages Foraging Behavior of Cabbage Butterfly, *Pieris rapae*", Journal of Chemical Ecology, Mar. 1, 2000, pp. 655-666, Springer, New York, US.

Tian, et al. "Electroantennographic Responses and Field Attraction to Peach Fruit Odors in the Fruit-Piercing Moth, Oraesia excavata (Butler) (Lepidoptera:Noctuidae)", Applied Entomology and Zoology, vol. 43, No. 1 Jan. 1, 2008 pp. 265-269, Springer, US.

Noshita et al. "Total Synthesis of Natural (+)-Phomopsolide B, an Antifeedant against Elm Bark Beetle", Bioscience Biotechnology Biochemiostry, vol. 58, No. 4 Jan. 1, 1994, pp. 740-744, Taylor and Francis, New York, US.

Extended European Search Report for the corresponding European application 17 18 0427.1, dated Feb. 28, 2018, 17 pages.

* cited by examiner

FEEDING DETERRENCE IN AGRICULTURAL PESTS SUCH AS HEMIPTERA, LEPIDOPTERA AND COLEOPTERA

FIELD OF THE INVENTION

This invention relates to the use of compounds as agents that deter feeding of crops by agricultural pests such as hemiptera, lepidoptera and coleoptera including, but not limited to, stink bugs, codling moth larvae and granary weevils.

The active feeding deterrence agents of this invention are an effective control agent against agricultural pests such as hemiptera, lepidoptera and coleoptera. Hemiptera includes cicadas, aphids and stink bugs such as the Brown Marmorated Stink Bug. Lepidoptera includes butterflies and moths such as the Codling Moth. Coleoptera are beetles and the order contains granary weevils.

BACKGROUND TO THE INVENTION

Agricultural pests including but not limited to the brown marmorated stink bug, codling moth and granary weevil are known to feed on various crops causing damage to fruits, vegetables and other plant life. The cost of this damage is extensive and leads to hardship among growers.

In the Mid-Atlantic region, where brown marmorated stink bugs are well established, they caused an estimated $37 million in damage in apple crops alone in 2010, the most recent year for which data are available. [Darryl Fears, "Stink bugs migrating to deep south", *Washington Post*, Mar. 16, 2012]. Aside from apples, the bug will feed on nearly anything, including cherries, tomatoes, grapes, lima beans, soybeans, green peppers and peaches.

Codling moth larvae penetrate into apples and pears and tunnel to the core, leaving holes in the fruit that are filled with reddish-brown, crumbly droppings. If left uncontrolled, larvae can cause substantial damage, often infesting 20 to 90% of the fruit, depending on the variety and location. Late maturing varieties are more likely to suffer severe damage than early varieties. [J. L. Caprile and P. M. Vossen, *Pest Notes*: Codling Moth UC ANR Publication 7412, May 2011].

In walnuts, codling moth larvae feed on the kernels. Nuts damaged early in the season when the nuts are quite small will drop off trees soon after damage occurs. Nuts damaged later in the season will remain on trees, but their kernels are inedible. Walnuts aren't as favored a host as apples and pears, and untreated trees might incur very little to modest damage (10 to 15% of the nuts), depending on the variety and location. [*Pest Notes*, May 2011]

Phosmet, a phthalimide-derived, non-systemic, organophosphate insecticide is the primary means of controlling codling moth damage to apples. This material is on the US Emergency Planning list of extremely hazardous substances and is highly toxic to bees. The materials covered in this patent application would be a much gentler means of deterring the larvae and controlling moth infestation.

Granary weevils are attracted to and will attack all kinds of grains and grain products. These products will include such materials as wheat, corn, barley, or rice. In stored food products, they may be found in materials like macaroni or spaghetti. Adult weevils will feed on the same foods as the larvae. However, because they do not need to develop in the inside of whole grains like larvae do, they are not limited to just one grain or in other words, they are not restricted in their diets. [http://www.pestmall.com/blog/pest-info/other-pests/granary-weevil-biology]

Control of weevils is quite difficult as they live and breed in our food sources. Use of pyrethrins is an option, but food shouldn't be sprayed directly. Use of our materials may be sprayed directly on crops, seeds, agricultural or ornamental trees, plants, vegetation, produce or packaging materials so they provide a better alternative to traditional insecticides.

SUMMARY OF THE INVENTION

In accordance with this invention, feeding deterrence of crops by agricultural pests such as hemiptera, lepidoptera and coleoptera is obtained by contact of the insects with at least one of the compounds of the structure (I)

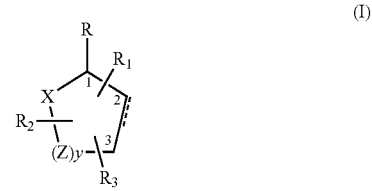

wherein:
R is selected from —OH, =O, —OC(O)$R_4$, —O$R_6$, and —(O$R_6$)$_2$, wherein each $R_6$ is independently selected from an alkyl group containing from 1 to 4 carbon atoms and $R_4$ is a branched or straight chain, saturated or unsaturated, hydrocarbyl group with zero to two double bonds and from 1 to 15 carbon atoms;
X is O or $CH_2$ with the proviso that when X is O R can only be =O;
each Z is independently selected from (CH) and ($CH_2$);
y is a numeral selected from 1 and 2;
$R_1$ is selected from H or a branched or straight chain, saturated or unsaturated hydrocarbyl group with zero to two double bonds and from 1 to 15 carbon atoms;
$R_2$ is selected from H and a branched or straight chain, saturated or unsaturated hydrocarbyl group with zero to three double bonds and from 1 to 15 carbon atoms;
$R_3$ is selected from H, a branched or straight chain, saturated or unsaturated hydrocarbyl group with zero to three double bonds and from 1 to 15 carbon atoms, —($CH_2$)$_n$OH, —C(O)O$R_5$, —$CH_2$C(O)O$R_7$, —$CH_2$C(O)$R_8$, —C(O)N$R_9R_{10}$, and —$CH_2$C(O)N$R_{11}R_{12}$ where each of $R_5$, $R_7$, $R_8$, $R_9$, $R_{10}$, $R_{11}$ and $R_{12}$ is independently selected from H and a branched or straight chain, saturated or unsaturated hydrocarbyl group with zero to three double bonds and from 1 to 15 carbon atoms and n is an integer of from 1 to 12;
the bond between the 2 and 3 positions in the ring structure may be a single or a double bond; and
wherein the compounds of structure (I) contain from 9 to 20 total carbon atoms in the compounds. The invention also includes optical isomers, diastereomers and enantiomers of the compounds of structure (I). Thus, at all stereocenters where stereochemistry is not explicitly defined, all possible epimers are envisioned.

The feeding deterrence compounds of this invention, which could be applied directly to crops, seeds, agricultural or ornamental trees, plants, vegetation, produce or packaging materials for crops, have low mammalian toxicity and are similar to naturally occurring materials used in flavor/fragrance applications. Therefore, these provide a better method of control for farmers and home owners. Additionally, the feeding deterrence compounds of this invention have the potential to be used on organic crops.

The compounds of structure (I) may be employed to defer feeding by agricultural pests such as hemiptera, lepidoptera and coleoptera which include, but are not limited to, stink bugs, codling moth larvae and granary weevils. The active compounds of structure (I) may be employed in any suitable formulation, such as, but not limited to, direct spray formulations, fogger formulations, microencapsulated formulations, soil treatment formulations, seed treatment formulations, injectable formulations for injection into the plant and formulations for use in evaporative devices.

DETAILED DESCRIPTION OF THE INVENTION

Deterrence of feeding by agricultural pests such as hemiptera, lepidoptera and coleoptera including, but not limited to, stink bugs, codling moth larvae and granary weevils is obtained by contact of the insects with at least one of the compounds of the structure (I)

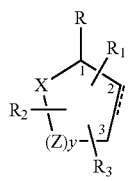

(I)

wherein
R is selected from —OH, =O, —OC(O)$R_4$, —$OR_6$, and —$(OR_6)_2$, wherein each $R_6$ is independently selected from an alkyl group containing from 1 to 4 carbon atoms and $R_4$ is a branched or straight chain, saturated or unsaturated hydrocarbyl group with zero to two double bonds and from 1 to 15 carbon atoms;
X is O or $CH_2$ with the proviso that when X is O R can only be =O;
each Z is independently selected from (CH) and ($CH_2$);
y is a numeral selected from 1 and 2;
$R_1$ is selected from H or a branched or straight chain, saturated or unsaturated hydrocarbyl group with zero to two double bonds and from 1 to 15 carbon atoms;
$R_2$ is selected from H and a branched or straight chain, saturated or unsaturated hydrocarbyl group with zero to three double bonds and from 1 to 15 carbon atoms;
$R_3$ is selected from H, a branched or straight chain, saturated or unsaturated hydrocarbyl group with zero to three double bonds and from 1 to 15 carbon atoms —$(CH_2)_n$OH, —C(O)$OR_5$, —$CH_2$C(O)$OR_7$, —$CH_2$C(O)$R_8$, —C(O)$NR_9R_{10}$, and —$CH_2$C(O)$NR_{11}R_{12}$ where each of $R_5$, $R_7$, $R_8$, $R_9$, $R_{10}$, $R_{11}$ and $R_{12}$ is independently selected from H and a branched or straight chain, saturated or unsaturated hydrocarbyl group with zero to three double bonds and from 1 to 15 carbon atoms, and n is n integer of from 1 to 12;
the bond between the 2 and 3 positions in the ring structure may be a single or a double bond; and
wherein the compounds of structure (1) contain from 11 to 20 total carbon atoms in the compounds. The invention also includes optical isomers, diastereomers and enantiomers of the named structures. Thus, at all stereocenters where stereochemistry is not explicitly defined, all possible epimers are envisioned.

A preferred group of feeding deterrence compounds are those compounds of Structure (I) wherein;
R is selected from —OH and =O, X is $CH_2$, y is 1 or 2, each Z is selected from (CH) and ($CH_2$), the bond between positions 2 and 3 in the ring is a single bond, one of $R_1$ and $R_2$ is H or —$CH_3$ and the other of $R_1$ and $R_2$ is a branched or straight chain, saturated or unsaturated hydrocarbyl group containing from 9 to 15 carbon atoms and 0 to 3 double bonds, and $R_3$ is H.

Another preferred group of feeding deterrence compounds are those compounds of structure (I) wherein;
R is selected from —OH and =O, more preferably =O, X is $CH_2$, y is 1 or 2, more preferably 1, each Z is selected from (CH) and ($CH_2$), the bond between positions 2 and 3 in the ring is a single or double bond, more preferably a single bond, one of $R_1$ and $R_2$ is H and the other of $R_1$ and $R_2$ is a branched or straight chain, saturated or unsaturated hydrocarbyl group containing from 9 to 15 carbon atoms and 0 to 3 double bonds, and $R_3$ is selected from —C(O)$OR_5$ and —$CH_2$C(O)$R_8$ where $R_5$ and $R_8$ are each selected from a straight chain or branched, saturated or unsaturated hydrocarbyl group containing from 1 to 6 carbon atoms, and more preferably 3 to 5 carbon atoms and still more preferably —$CH_3$.

Another preferred group of feeding deterrence compounds are those compounds of structure (I) wherein
R is =O, X is O, y is 1 or 2, each Z is selected from (CH) and ($CH_2$), the bond between positions 2 and 3 of the rings is a single or double bond, more preferably a single bond, one of $R_1$ and $R_2$ is H and the other of $R_1$ and $R_2$ is a branched or straight chain, saturated or unsaturated hydrocarbyl group containing from 9 to 15 carbon atoms and 0 to 3 double bonds, and $R_3$ is selected from —C(O)$OR_5$ and —$CH_2$C(O)$R_8$ where $R_5$ and $R_7$ are each selected from a hydrocarbyl group containing from 1 to 6 carbon atoms, and more preferably 3 to 5 carbon atoms and still more preferably —$CH_3$ and wherein the total number of carbon atoms in the compounds of structure (I) is from 9 to 20, more preferably from 9 to 14 total carbon atoms.

Another preferred group of feeding deterrence compounds are those compounds of structure (I) wherein
R is =O, X is O, y is 1 or 2, each Z is selected from (CH) and ($CH_2$), the bond between positions 2 and 3 in the ring is a single bond, $R_1$ is a branched or straight chain, saturated or unsaturated alkyl group containing from 5 to 13 carbon atoms, $R_2$ is H or —$CH_3$, $R_3$ is H, and more preferably where $R_1$ is an alkyl group of from 5 to 10 carbon atoms such that the compound of structure (I) contains from 11 to 14 total carbon atoms.

The active compounds of structure (I) may be employed in any suitable formulation, such as, but not limited to, direct spray formulations, fogger formulations, microencapsulated formulations, soil treatment formulations, seed treatment formulations, injectable formulation for injection into the plant and formulations for use in evaporative devices. The formulations of the active compounds will be such that the food or crops being treated will have from about 0.05 to about 250 mg/sq. in., preferably about 0.25 to about 50 mg/sq. in., of the active compounds thereon.

Representative examples of compounds of structure (I) include, but are not limited to,

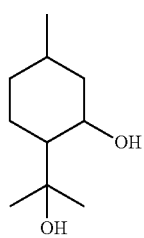

Cyclohexanementhanol, 2-hydroxy-a,a,4-trimethyl-
Chemical Formula: $C_{10}H_{20}$
Molecular Weight: 172.26
Para-Menthane-3,8-Diol (PMD)

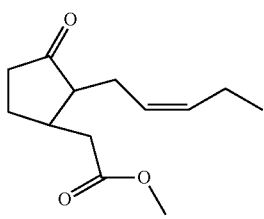

(Z)-methyl 2-(3-oxo-2-(pent-2-enyl)cyclopentyl)acetate
Chemical Formula: $C_{13}H_{20}O_3$
Molecular Weight: 224.30
Methyl Jasmonate

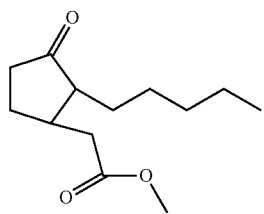

methyl 2-(3-oxo-2-pentylcyclopentyl)acetate
Chemical Formula: $C_{13}H_{22}O_3$
Molecular Weight: 226.31
Methyl Dihydro Jasmonate

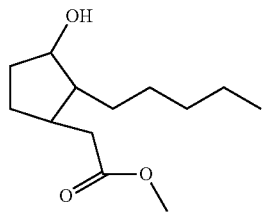

methyl 2-(3-hydroxy-2-pentylcyclopentyl)acetate
Chemical Formula: $C_{13}H_{24}O_3$
Molecular Weight: 228.33
Methyl Dihydro Jasmolate

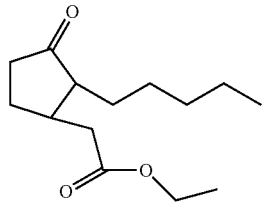

ethyl 2-(3-oxo-2-pentylcyclopentyl)acetate
Chemical Formula: $C_{14}H_{24}O_3$
Molecular Weight: 240.34
Ethyl Dihydro Jasmonate -continued

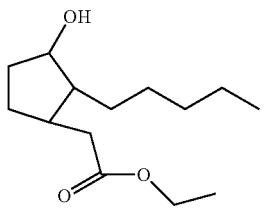

ethyl 2-(3-hydroxy-2-pentylcyclopentyl)acetate
Chemical Formula: $C_{14}H_{26}O_3$
Molecular Weight: 242.35
Ethyl Dihydro Jasmolate

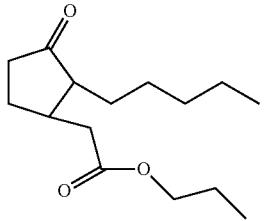

propyl 2-(3-oxo-2-pentylcyclopentyl)acetate
Chemical Formula: $C_{15}H_{26}O_3$
Molecular Weight: 254.37
Propyl Dihydro Jasmonate

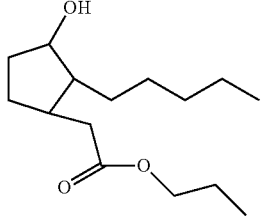

propyl 2-(3-hydroxy-2-pentylcyclopentyl)acetate
Chemical Formula: $C_{15}H_{28}O_3$
Molecular Weight: 256.38
Propyl Dihydro Jasmolate

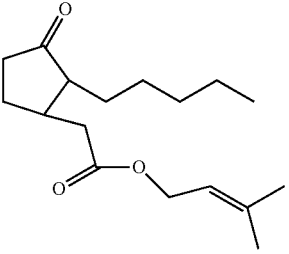

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

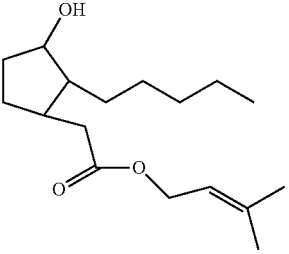

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

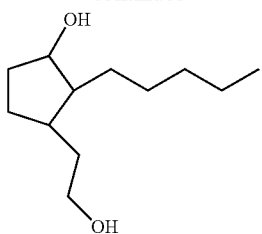

3-(2-hydroxyethyl)-2-pentylcyclopentanol
Chemical Formula: $C_{12}H_{24}O_2$
Molecular Weight: 200.32
MethylDihydroJasmodiol

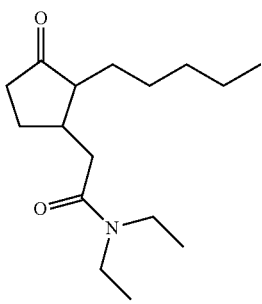

N,N-diethyl-2-(3-oxo-2-pentylcyclopentyl)acetamide
Chemical Formula: $C_{16}H_{29}NO_2$
Molecular Weight: 267.41
MDJ Amide

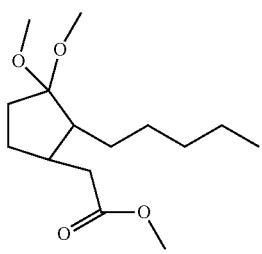

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

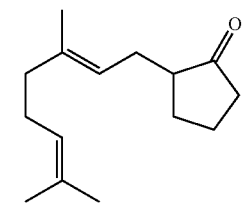

(E)-2-(3,7-dimethylocta-2,6-dienyl)cyclopentanone
Chemical Formula: $C_{15}H_{24}O$
Molecular Weight: 220.35
Apritone

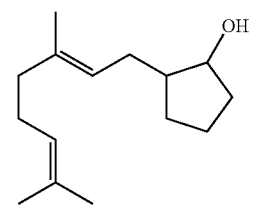

(E)-2-(3,7-dimethylocta-2,6-dienyl)cyclopentanol
Chemical Formula: $C_{15}H_{26}O$
Molecular Weight: 222.37
Apritol

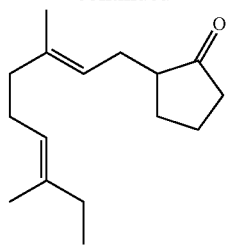

2-((2E,6E)-3,7-dimethylnona-2,6-dienyl)cyclopentanone
Chemical Formula: $C_{16}H_{26}O$
Molecular Weight: 234.38
Methyl Apritone

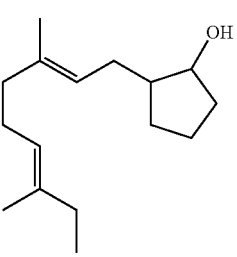

2-((2E,6E)-3,7-dimethylnona-2,6-dienyl)cyclopentanol
Chemical Formula: $C_{16}H_{28}O$
Molecular Weight: 236.39
Methyl Apritol

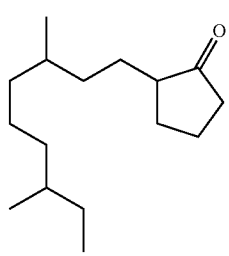

2-(3,7-dimethylnonyl)cyclopentanone
Chemical Formula: $C_{16}H_{30}O$
Molecular Weight: 238.41
Tetrahydromethyl Apritone

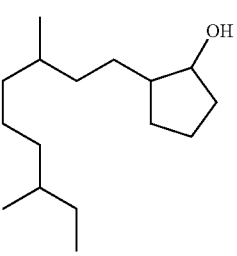

2-(3,7-dimethylnonyl)cyclopentanol
Chemical Formula: $C_{16}H_{32}O$
Molecular Weight: 240.42
Tetrahydromethyl Apritol

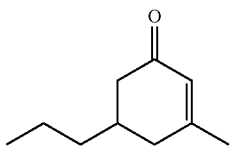

2-Cyclohexen-1-one, 3-methyl-5-propyl-
Chemical Formula: $C_{10}H_{16}O$
Molecular Weight: 152.23

-continued

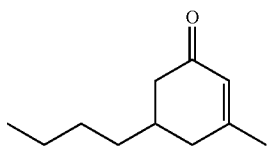

5-Butyl-3-methyl-2-cyclohexenone
Chemical Formula: $C_{11}H_{18}O$
Molecular Weight: 166.26

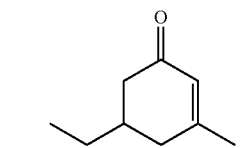

5-Ethyl-3-methyl-2-cyclohexenone
Chemical Formula: $C_9H_{14}O$
Molecular Weight: 138.21

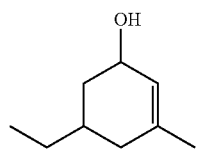

5-Ethyl-3-methyl-2-cyclohexen-1-ol
Chemical Formula: $C_9H_{16}O$
Molecular Weight: 140.22

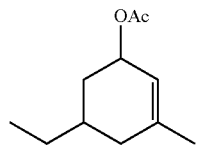

5-Ethyl-3-methyl-2-cyclohexen-1-yl Acetate
Chemical Formula: $C_{11}H_{18}O_2$
Molecular Weight: 182.26

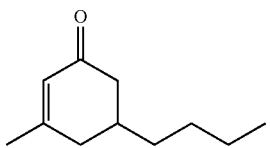

Chemical Formula: $C_{11}H_{18}O$
Molecular Weight: 166.26
3-methyl-5-butyl-2-cyclohexenone

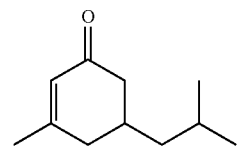

Chemical Formula: $C_{11}H_{18}O$
Molecular Weight: 166.26
3-methyl-5-isobutyl-2-cyclohexenone

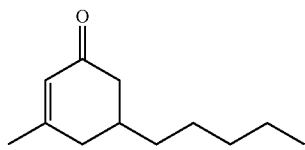

Chemical Formula: $C_{12}H_{20}O$
Molecular Weight: 180.29
3-methyl-5-pentyl-2-cyclohexenone

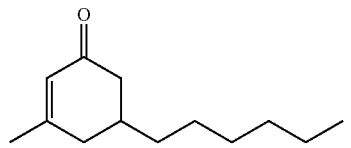

Chemical Formula: $C_{13}H_{22}O$
Molecular Weight: 194.31
3-methyl-5-hexyl-2-cyclohexenone

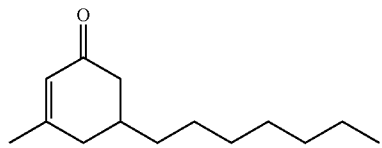

Chemical Formula: $C_{14}H_{24}O$
Molecular Weight: 208.34
3-methyl-5-heptyl-2-cyclohexenone -continued

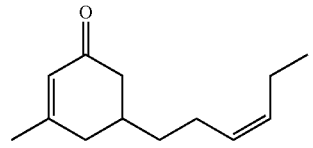

Chemical Formula: $C_{13}H_{20}O$
Molecular Weight: 192.30
3-methyl-5-(z-3-hexenyl)-2-cyclohexenone

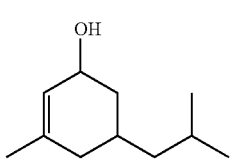

Chemical Formula: $C_{11}H_{20}O$
Molecular Weight: 168.28
3-methyl-5-isobutyl-2-cyclohexen-1-ol

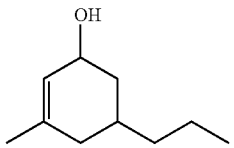

Chemical Formula: $C_{10}H_{18}O$
Molecular Weight: 154.25
3-methyl-5-propyl-2-cyclohexen-1-ol

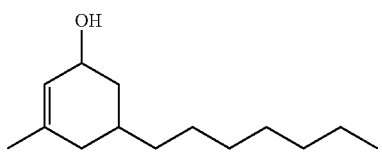

Chemical Formula: $C_{14}H_{26}O$
Molecular Weight: 210.36
3-methyl-5-heptyl-2-cyclohexen-1-ol

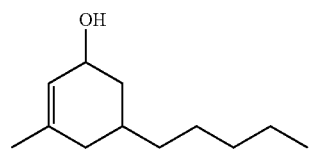

Chemical Formula: $C_{12}H_{22}O$
Molecular Weight: 182.30
3-methyl-5-pentyl-2-cyclohexen-1-ol

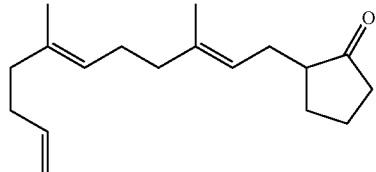

2-((2E,6E)-3,7,11-trimethyldodeca-2,6,10-trienyl)cyclopentanone
Chemical Formula: $C_{20}H_{32}O$
Molecular Weight: 288.47
Farnesylcyclopentanone -continued

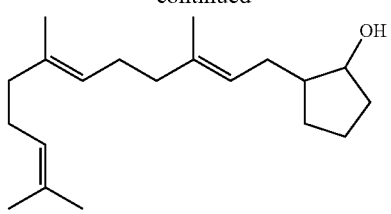

2-((2E,6E)-3,7,11-trimethyldodeca-2,6,10-trienyl)cyclopentanol
Chemical Formula: C$_{20}$H$_{34}$O
Molecular Weight: 290.48
Farnesylcyclopentanol

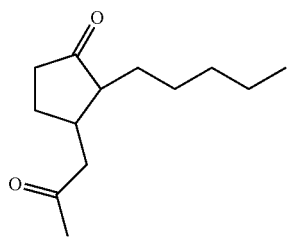

3-(2-oxopropyl)-2-pentylcyclopentanone
Chemical Formula: C$_{13}$H$_{22}$O$_2$
Molecular Weight: 210.31
Amyl Cyclopentanone Propanone

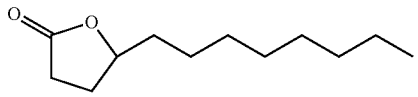

5-octyldihydrofuran-2(3H)-one
Chemical Formula: C$_{12}$H$_{22}$O$_2$
Molecular Weight: 198.30
gamma-dodecalactone

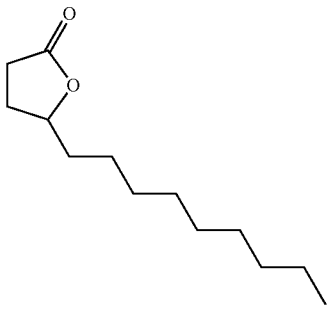

5-nonyldihydrofuran-2(3H)-one
Chemical Formula: C$_{13}$H$_{24}$O$_2$
Molecular Weight: 212.33
Gamma-Tridecalactone

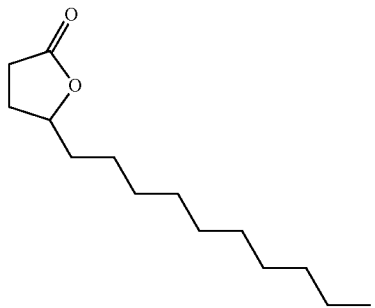

5-decyldihydrofuran-2(3H)-one
Chemical Formula: C$_{14}$H$_{26}$O$_2$
Molecular Weight: 226.36
Gamma-Tetradecalactone -continued

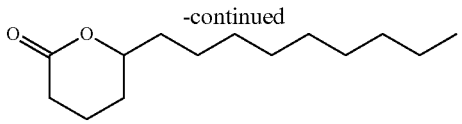

6-nonyltetrahydro-2H-pyran-2-one
Chemical Formula: C$_{14}$H$_{26}$O$_2$
Molecular Weight: 226.36
Delta-Tetradecalactone

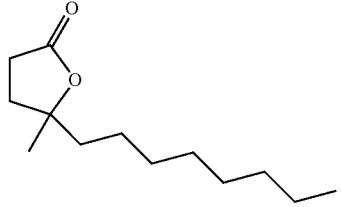

Gamma Methyl Dodecalactone
2(3H)-Furanone, 5-octyldihydro-5-methyl-

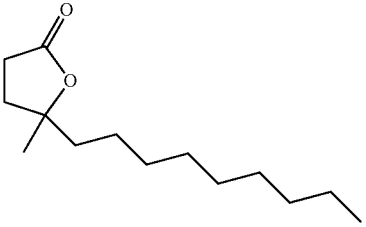

gamma Methyl Tridecalactone
5-methyl-5-nonyldihydrofuran-2(3H)-one
4-methyl-4-nonyl gamma butyrolactone
C$_{14}$ lactone Preferred compounds of structure (I) include methyl apritone, methyl dihydrojasmonate, propyl dihydrojasmonate, gamma-dodecalactone, gamma-tridecalactone, gamma methyl dodecalactone, gamma methyl tridecalactone, 3-methyl-5-propyl-2-cyclohexenone, 3-methyl-5-isobutyl-2-cyclohexenone, 3-methyl-5-isobutyl-2-cyclohexenol, 3-methyl-5-pentyl-2-cyclohexenone and 3-methyl-5-heptyl-2-cyclohexenone.

A test was designed to measure the repellency as feeding deterrence in brown marmorated stink bugs (BMSB). Five replicates of 5 BMSBs were introduced into test arenas, containing one 60 mm×15 mm Petri dish with treated filter papers in which a food source (green bean) was attached, at the start of the test. The small Petri dishes containing the treated filter paper and food source were covered with a fitted Petri dish lid in between observation times, and were removed 5 minutes before each observation time to prevent stink bugs from feeding until sated. The distribution of the BMSBs was observed and documented hourly for 5 hours.

TABLE 1

| Compound in a 57% Ethanol:43% water solution | Repellency averaged over 5 hours |
|---|---|
| Control (57% Ethanol:43% water solution) | 38% |
| Methyl Dihydrojasmonate (3.5%) | 90% |
| Methyl Dihydrojasmonate - Low epi (2.5%) | 58% |
| Methyl Dihydrojasmonate - High epi (2.5%) | 39% |
| Propyl Dihydrojasmonate (3.5%) | 100% |
| Propyl Dihydrojasmonate - Low epi (2.5%) | 74% |
| Propyl Dihydrojasmonate - High epi (2.5%) | 49% |
| Para-Menthanediol (3.5%) | 91% |
| Gamma-Dodecalactone (3.5%) | 82% |
| Gamma-Methyl Tridecalactone (3.5%) | 67% |

Another test was designed to measure the repellency as feeding deterrence in Codling Moth larvae. The treatment was applied to the surface of a proprietary laboratory media in a tray with wells for each compound. The media was allowed to dry for 30-60 minutes so that larvae were not exposed to it as a liquid. One first instar codling moth larva was then placed on the treated media. The cover film was placed on the tray to prevent escapes. Ten additional replicates treated with a 57% ethanol solution were prepared to serve as controls. The larvae were observed at 24 hours to determine if they burrowed into the media. After the 24 hour reading, the larvae were extracted from the media to record any mortality.

TABLE 2

| Compound at 3.5% in a 57% Ethanol:43% water solution | Repellency at 24 hours |
| --- | --- |
| Control (57% Ethanol:43% water solution) | 8% |
| Para-Menthanediol | 10% |
| Propyl Dihydrojasmonate | 59% |
| Prenyl Dihydrojasmonate | 79% |
| Gamma-Dodecalactone | 46% |
| Methyl Apritone | 100% |
| 3-Methyl-5-Propyl-2-Cyclohexenone | 21% |
| 3-Methyl-5-Propyl-2-Cyclohexenol | 30% |
| 3-Methyl-5-Heptyl-2-Cyclohexenone | 95% |

Mortality observations were also made for the above protocol. The control was the 57% ethanol:43% water solution.

TABLE 3

| Compound at 3.5% in a 57% Ethanol:43% water solution | Increased Mortality over Control Mortality at 24 hours |
| --- | --- |
| Para-Menthanediol | 3% |
| Propyl Dihydrojasmonate | 18% |
| Prenyl Dihydrojasmonate | 34% |
| Gamma-Dodecalactone | 37% |
| Methyl Apritone | 95% |
| 3-Methyl-5-Propyl-2-Cyclohexenone | 1% |
| 3-Methyl-5-Propyl-2-Cyclohexenol | 9% |
| 3-Methyl-5-Heptyl-2-Cyclohexenone | 93% |

Ten replicates of 30 kernels of wheat were immersed into the test compound and allowed to dry for 24 hours. The grains were then transferred to a test container, and 10 granary weevils were released. Test containers were secured and left for a 3 week period. At the end of this time, the wheat grains were examined for developing larvae and damage by larvae. The number of grains that contained developing larvae or that showed damage was recorded. Ten additional replicates treated with isopropyl alcohol were prepared to serve as controls.

TABLE 4

| Test compound, diluted in isopropyl alcohol | Increased Repellency vs. Control Repellency | Increased Mortality over Control Mortality |
| --- | --- | --- |
| Methyl Apritone (5%) | 11% | N/A |
| Propyl Dihydrojasmonate (5%) | 8% | N/A |
| Gamma Tridecalactone (5%) | 40% | N/A |
| 3-Methyl-5-Propyl-2-Cyclohexenone (5%) | 66% | 57% |
| 3-Methyl-5-Isobutyl-2-Cyclohexenol (5%) | 86% | 93% |

The feeding deterrent compounds of this invention may be blended with active repellents or toxicants including, but not limited to, N,N-Diethyl-m-toluamide (DEET®) and p-Menthane-3,8-diol (PMD).

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

I claim:

1. A method for deterring the feeding of one or more agricultural pests selected from the group consisting of stink bugs, codling moth larvae and granary weevils on food or crops is obtained by:

contacting of the pests with an effective amount of a formulation consisting essentially of at least one of the compounds selected from the group consisting of:

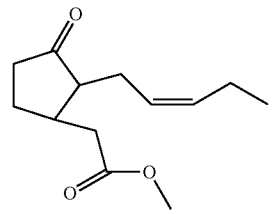

(Z)-methyl 2-(3-oxo-2-(pent-2-enyl)cyclopentyl)acetate
Chemical Formula: $C_{13}H_{20}O_3$
Molecular Weight: 224.30
Methyl Jasmonate

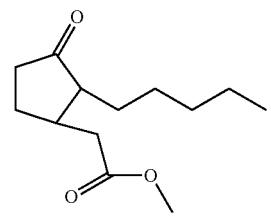

methyl 2-(3-oxo-2-pentylcyclopentyl)acetate
Chemical Formula: $C_{13}H_{22}O_3$
Molecular Weight: 226.31
Methyl Dihydro Jasmonate

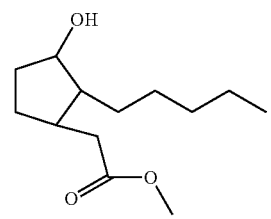

methyl 2-(3-hydroxy-2-pentylcyclopentyl)acetate
Chemical Formula: $C_{13}H_{24}O_3$
Molecular Weight: 228.33
Methyl Dihydro Jasmolate -continued

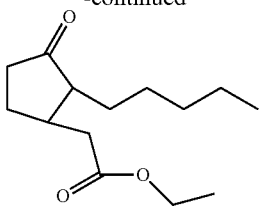

ethyl 2-(3-oxo-2-pentylcyclopentyl)acetate
Chemical Formula: $C_{14}H_{24}O_3$
Molecular Weight: 240.34
Ethyl Dihydro Jasmonate

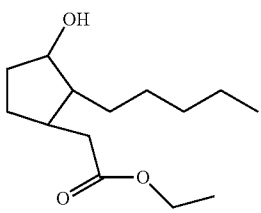

ethyl 2-(3-hydroxy-2-pentylcyclopentyl)acetate
Chemical Formula: $C_{14}H_{26}O_3$
Molecular Weight: 242.35
Ethyl Dihydro Jasmolate

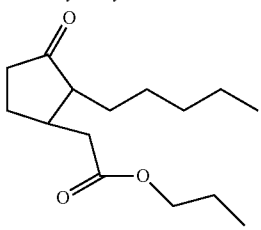

propyl 2-(3-oxo-2-pentylcyclopentyl)acetate
Chemical Formula: $C_{15}H_{26}O_3$
Molecular Weight: 254.37
Propyl Dihydro Jasmonate

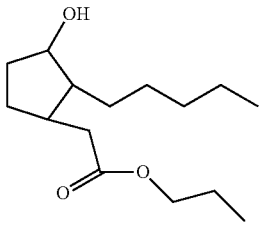

propyl 2-(3-hydroxy-2-pentylcyclopentyl)acetate
Chemical Formula: $C_{15}H_{28}O_3$
Molecular Weight: 256.38
Propyl Dihydro Jasmolate

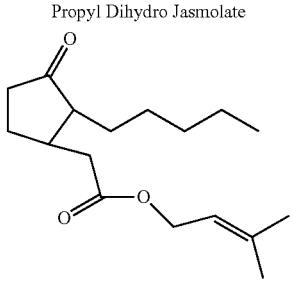

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate -continued

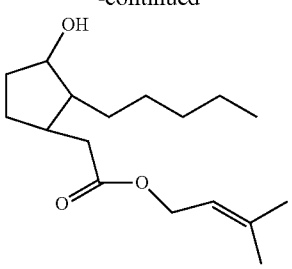

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

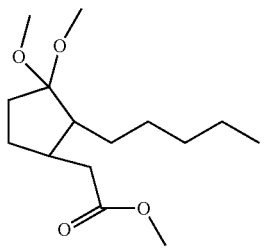

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

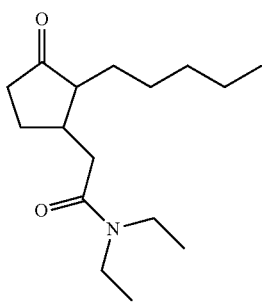

and

N,N-diethyl-2-(3-oxo-2-pentylcyclopentyl)acetamide
Chemical Formula: $C_{16}H_{29}NO_2$
Molecular Weight: 267.41
MDJ Amide

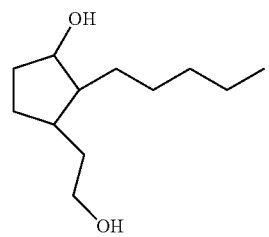

3-(2-hydroxyethyl)-2-pentylcyclopentanol
Chemical Formula: $C_{12}H_{24}O_2$
Molecular Weight: 200.32
MethylDihydroJasmodiol wherein at least one of the compounds is present in said formulation in an amount sufficient to provide increased pest repellency or mortality over control pest repellency or mortality of at least 1%.

2. A method for deterring the feeding of one or more agricultural pests selected from the group consisting of stink bugs, codling moth larvae and granary weevils on food or crops is obtained by:

contacting of the pests with an effective amount of a formulation consisting essentially of at least one of the compounds selected from the group consisting of:

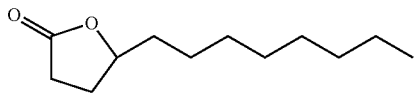

5-octyldihydrofuran-2(3H)-one
Chemical Formula: $C_{12}H_{22}O_2$
Molecular Weight: 198.30
Gamma-dodecalactone

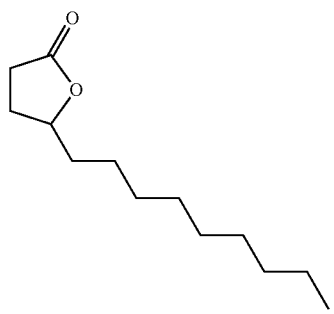

5-nonyldihydrofuran-2(3H)-one
Chemical Formula: $C_{13}H_{24}O_2$
Molecular Weight: 212.33
Gamma-Tridecalactone

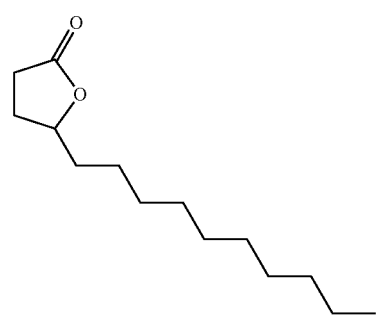

5-decyldihydrofuran-2(3H)-one
Chemical Formula: $C_{14}H_{26}O_2$
Molecular Weight: 226.36
Gamma-Tetradecalactone

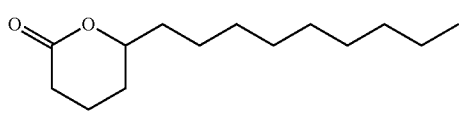

6-nonyltetrahydro-2H-pyran-2-one
Chemical Formula: $C_{14}H_{26}O_2$
Molecular Weight: 226.36
Delta-Tetradecalactone

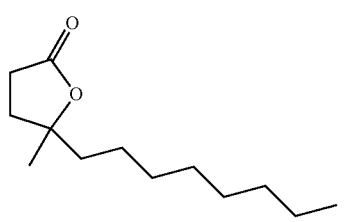

and

Gamma Methyl Dodecalactone
2(3H)-Furanone, 5-octyldihydro-5-methyl

-continued

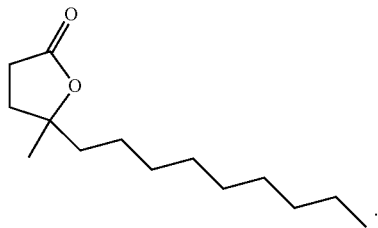

Gamma Methyl Tridecalactone
5-methyl-5-nonyldihydrofuran-2(3H)-one
4-methyl-4-nonyl gamma butyrolactone
C14 lactone wherein at least one of the compounds is present in said formulation in an amount sufficient to provide increased pest repellency or mortality over control pest repellency or mortality of at least 1%.

3. A method for deterring the feeding of one or more agricultural pests selected from the group consisting of stink bugs, codling moth larvae and granary weevils on food or crops is obtained by:

contacting of the pests with an effective amount of a formulation consisting essentially of at least one of the compounds selected from the group consisting of:

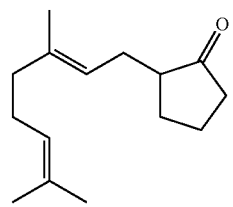

(E)-2-(3,7-dimethylocta-2,6-dienyl)cyclopentanone
Chemical Formula: $C_{15}H_{24}O$
Molecular Weight: 220.35
Apritone

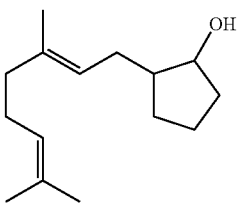

(E)-2-(3,7-dimethylocta-2,6-dienyl)cyclopentanol
Chemical Formula: $C_{15}H_{26}O$
Molecular Weight: 222.37
Apritol

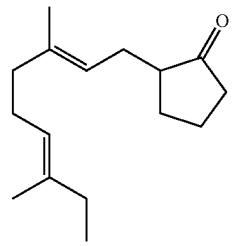

2-((2E,6E)-3,7-dimethylnona-2,6-dienyl)cyclopentanone
Chemical Formula: $C_{16}H_{26}O$
Molecular Weight: 234.38
Methyl Apritone

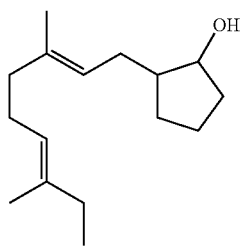

2-((2E,6E)-3,7-dimethylnona-2,6-dienyl)cyclopentanol
Chemical Formula: $C_{16}H_{28}O$
Molecular Weight: 236.39
Methyl Apritol

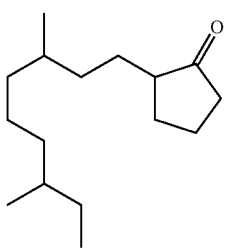

2-(3,7-dimethylnonyl)cyclopentanone
Chemical Formula: $C_{16}H_{30}O$
Molecular Weight: 238.41
Tetrahydromethyl Apritone

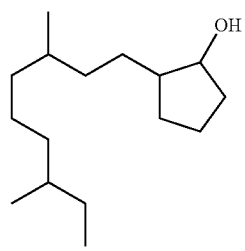

2-(3,7-dimethylnonyl)cyclopentanol
Chemical Formula: $C_{16}H_{32}O$
Molecular Weight: 240.42
Tetrahydromethyl Apritol wherein at least one of the compounds is present in said formulation in an amount sufficient to provide increased pest repellency or mortality over control pest repellency or mortality of at least 1%.

4. A method for deterring the feeding of one or more agricultural pests selected from the group consisting of stink bugs, codling moth larvae and granary weevils on food or crops is obtained by:

contacting of the pests with an effective amount of a formulation consisting essentially of at least one of the compounds selected from the group consisting of:

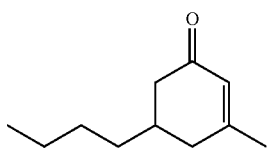

5-Butyl-3-methyl-2-cyclohexenone
Chemical Formula: $C_{11}H_{18}O$
Molecular Weight: 166.26

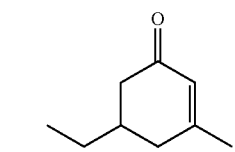

5-Ethyl-3-methyl-2-cyclohexenone
Chemical Formula: $C_9H_{14}O$
Molecular Weight: 138.21

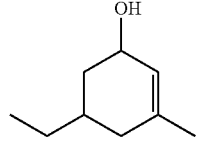

5-Ethyl-3-methyl-2-cyclohexen-1-ol
Chemical Formula: $C_9H_{16}O$
Molecular Weight: 140.22

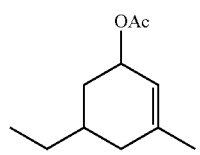

5-Ethyl-3-methyl-2-cyclohexen-1-yl Acetate
Chemical Formula: $C_{11}H_{18}O_2$
Molecular Weight: 182.26

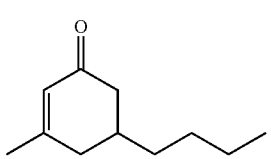 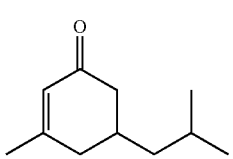

Chemical Formula: $C_{11}H_{18}O$  Chemical Formula: $C_{11}H_{18}O$
Molecular Weight: 166.26  Molecular Weight: 166.26
3-methyl-5-butyl-2-cyclohexenone  3-methyl-5-isobutyl-2-cyclohexenone

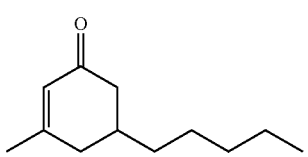

Chemical Formula: $C_{12}H_{20}O$
Molecular Weight: 180.29
3-methyl-5-pentyl-2-cyclohexenone

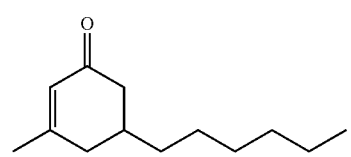

Chemical Formula: $C_{13}H_{22}O$
Molecular Weight: 194.31
3-methyl-5-hexyl-2-cyclohexenone

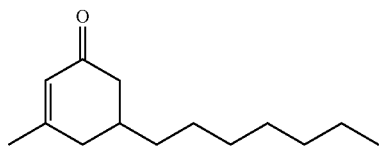

Chemical Formula: $C_{14}H_{24}O$
Molecular Weight: 208.34
3-methyl-5-heptyl-2-cyclohexenone

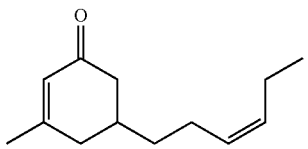

Chemical Formula: $C_{13}H_{20}O$
Molecular Weight: 192.30
3-methyl-5-(Z-3-hexenyl)-2-cyclohexenone

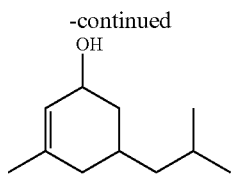

Chemical Formula: $C_{11}H_{20}O$
Molecular Weight: 168.28
3-methyl-5-isobutyl-2-cyclohexen-1-ol

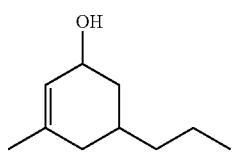

Chemical Formula: $C_{10}H_{18}O$
Molecular Weight: 154.25
3-methyl-5-propyl-2-cyclohexen-1-ol

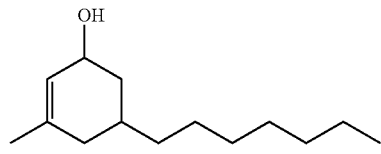

Chemical Formula: $C_{14}H_{26}O$
Molecular Weight: 210.36
3-methyl-5-heptyl-2-cyclohexen-1-ol

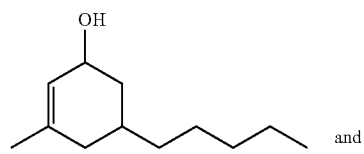

and

Chemical Formula: $C_{12}H_{22}O$
Molecular Weight: 182.30
3-methyl-5-pentyl-2-cyclohexen-1-ol

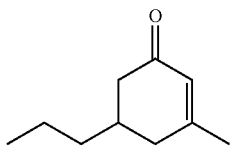

2-Cyclohexen-1-one, 3-methyl-5-propyl-
Chemical Formula: $C_{10}H_{16}O$
Molecular Weight: 152.23 wherein at least one of the compounds is present in said formulation in an amount sufficient to provide increased pest repellency or mortality over control pest repellency or mortality of at least 1%.

5. A method for deterring the feeding of one or more agricultural pests selected from the group consisting of stink bugs, codling moth larvae and granary weevils on food or crops is obtained by:

contacting of the pests with an effective amount of a formulation consisting essentially of at least one of the compounds selected from the group consisting of:

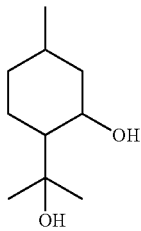

Cyclohexanemethanol, 2-hydroxy-a,a,4-trimethyl
Chemical Formula: $C_{10}H_{20}$
Molecular Weight: 172.26
Para-Menthane-3,8-Diol (PMD)

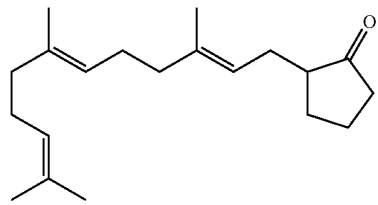

2-((2E,6E)-3,7,11-trimethyldodeca-2,6,10-trienyl)cyclopentanone
Chemical Formula: $C_{20}H_{32}O$
Molecular Weight: 288.47
Farnesylcyclopentanone

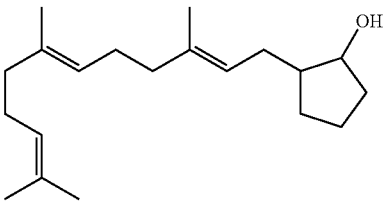

2-((2E,6E)-3,7,11-trimethyldodeca-2,6,10-trienyl)cyclopentanol
Chemical Formula: $C_{20}H_{34}O$
Molecular Weight: 290.48
Farnesylcyclopentanol

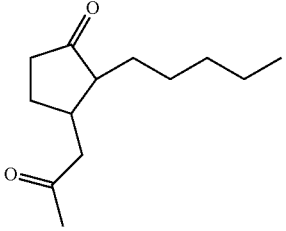

3-(2-oxopropyl)-2-pentylcyclopentanone
Chemical Formula: $C_{13}H_{22}O_2$
Molecular Weight: 210.31
Amyl Cyclopentanone Propanone wherein at least one of the compounds is present in said formulation in an amount sufficient to provide increased pest repellency or mortality over control pest repellency or mortality of at least 1%.

6. The method according to claim 1 wherein the at least one of the compounds is applied to crops, agricultural or ornamental trees, plants, vegetation, produce or packaging materials for plants or crops by way of a formulation selected from the group consisting of direct spray formulations, fogger formulations, microencapsulated formulations, soil treatment formulations, seed treatment formulations, injectable formulations for injection into or onto plants or crops, and formulations for evaporative devices.

7. A method for deterring the feeding of one or more agricultural pests selected from the group consisting of stink bugs, codling moth larvae and granary weevils on food or crops is obtained by:

contacting of the pests with an effective amount of a formulation consisting essentially of at least one of the compounds selected from the group consisting of: methyl apritone, methyl dihydrojasmonate, propyl dihydrojasmonate, gamma-dodecalactone, gamma-tridecalactone, gamma methyl dodecalactone, gamma methyl tridecalactone, 3-methyl-5-propyl-2-cyclohexenone, 3-methyl-5-isobutyl-2-cyclohexenone, 3-methyl-5-isobutyl-2-cyclohexenol, 3-methyl-5-pentyl-2-cyclohexenone and 3-methyl-5-heptyl-2-cyclohexenone;

wherein at least one of the compounds is present in said formulation in an amount sufficient to provide increased pest repellency or mortality over control pest repellency or mortality of at least 1%.

8. The method of claim 1 wherein the formulation further comprises a carrier.

9. The method of claim 1 wherein the formulation is used to treat food or crops such that the treated food or crops have from about 0.05 to about 250 mg/sq. in. of at least one of the compounds thereon.

* * * * *